United States Patent [19]

Rollmann et al.

[11] 4,108,881

[45] Aug. 22, 1978

[54] SYNTHESIS OF ZEOLITE ZSM-11

[75] Inventors: Louis Deane Rollmann, Princeton, N.J.; Ernest William Valyocsik, Yardley, Pa.

[73] Assignee: Mobil Oil Corporation, New York, N.Y.

[21] Appl. No.: 820,992

[22] Filed: Aug. 1, 1977

[51] Int. Cl.² .......................... C07F 5/06; C01B 33/28
[52] U.S. Cl. ............................ 260/448 C; 252/431 N; 252/455 Z; 423/328; 423/329
[58] Field of Search ................................ 423/328–330, 423/118; 260/448 C; 252/431 N, 455 Z

[56] References Cited

U.S. PATENT DOCUMENTS

| 3,709,979 | 1/1973 | Chu ...................................... 423/328 |
| 3,804,746 | 4/1974 | Chu ...................................... 208/111 |
| 4,016,245 | 4/1977 | Plank et al. ...................... 423/329 X |
| 4,025,571 | 5/1977 | Lago ................................. 423/328 X |
| 4,046,859 | 9/1977 | Plank et al. ......................... 423/328 |

*Primary Examiner*—Edward J. Meros
*Attorney, Agent, or Firm*—Charles A. Huggett; Raymond W. Barclay; Dennis P. Santini

[57] ABSTRACT

As synthesized by conventional technique, zeolite ZSM-11 is crystallized in the presence of substantial amount of at least one of the quaternary cations of a Group VA element of the Periodic Table of Elements. When synthesized in the conventional way, ZSM-11 contains said cations as well as substantial amount of sodium ions. To obtain a more catalytically active form of ZSM-11, the sodium ions must be exchanged to very low levels. By synthesizing zeolite ZSM-11 according to the present method, i.e. in the presence of one or more alkylenediamines having from 7 to 12 carbon atoms and with a specifically defined reaction mixture composition, ZSM-11 having different organic cations but the same crystal structure as conventionally prepared ZSM-11 is obtained. The ZSM-11 prepared in accordance hereto is very low in sodium content as synthesized.

17 Claims, No Drawings

SYNTHESIS OF ZEOLITE ZSM-11

BACKGROUND OF THE INVENTION

1. Field of the Invention

The present invention relates to a new form of ZSM-11, to a process for preparing it and to a method for using it in organic compound, e.g. hydrocarbon compound, conversion reactions. More particularly, it relates to making and using ZSM-11 which, in its as synthesized form, has different organic cations, extremely low sodium content and the same crystal structure as conventionally synthesized ZSM-11.

2. Summary of the Prior Art

Zeolite ZSM-11 is a relatively new zeolite which in its conventionally synthesized aluminosilicate form has the following composition expressed in terms of mole ratios of oxides in the anhydrous state:

$$(0.9 \pm 0.3)M_{2/n}O : Al_2O_3 : xSiO_2$$

wherein M is a mixture of at least one of the quaternary cations of Group VA of the Periodic Table, such as tetrabutylammonium or tetrabutylphosphonium, and alkali metal cations, especially sodium, n is the valence of M and $x$ is from 10 to 150. ZSM-11 has a distinctive X-ray diffraction pattern which further identifies it from other known zeolites. The original alkali metal cations of ZSM-11 can be exchanged by ion exchange with other ions to form species of the zeolite which have catalytic properties. Zeolite ZSM-11 and its conventional preparation are the subject of U.S. Pat. No. 3,709,979, the disclosure of which is incorporated herein by reference.

SUMMARY OF THE INVENTION

In accordance with the present invention there is provided a new form of zeolite ZSM-11 having the following formula in terms of mole ratios of oxides in the anhydrous state:

$$(0.5-10.0)R : (0-0.5)M_2O : Al_2O_3 : xSiO_2$$

wherein M is an alkali metal ion, especially sodium, and R is an alkylenediamine, especially a polymethylenediamine, having from 7 to 12 carbon atoms, or an organic nitrogen-containing cation derived therefrom and $x$ is from 10 to 1000. The present invention also provides a process for preparing the ZSM-11 and a method for using it in organic compound, e.g. hydrocarbon compound, conversion reactions.

DESCRIPTION OF SPECIFIC EMBODIMENTS

Zeolite ZSM-11 has been conventionally prepared by forming a mixture of alumina, silica, alkali metal oxide, water and a quaternary compound of a Group VA element such that the mixture has a composition, in terms of mole ratios of oxides, falling within the following range:

$SiO_2/Al_2O_3 = 10-150$
$H_2O/SiO_2 = 2.5-560$
$OH^-/SiO_2 = 0.05-2.0$
$M/SiO_2 = 0.1-1.4$
$R'/SiO_2 = 0.04-0.4$ wherein M is an alkali metal ion and R' is a quaternary cation of a Group VA element. The reaction mixture is maintained at a temperature of from about 100° C to about 200° C until crystals of ZSM-11 are formed.

Zeolite ZSM-11 possesses a definite distinguishing crystalline structure whose X-ray diffraction pattern shows the following significant lines:

TABLE I

| Interplanar Spacing d (A) | Relative Intensity |
| --- | --- |
| 11.2 ± .2 | Medium |
| 10.1 ± .2 | Medium |
| 6.73 ± .2 | Weak |
| 5.75 ± .1 | Weak |
| 5.61 ± .1 | Weak |
| 5.03 ± .1 | Weak |
| 4.62 ± .1 | Weak |
| 4.39 ± .08 | Weak |
| 3.86 ± .07 | Very Strong |
| 3.73 ± .07 | Medium |
| 3.49 ± .07 | Weak |
| (3.07, 3.00) ± .05 | Weak |
| 2.01 ± .02 | Weak |

The parenthesis around lines 3.07 and 3.00 indicate that they are separate and distinct lines, but are often superimposed. These values were determined by standard techniques. The radiation was the K-alpha doublet of copper, and a Geiger counter spectrometer with a strip chart pen recorder was used. The peak heights, I, and the positions as a function of 2 times theta, where theta is the Bragg angle, were read from the spectrometer chart. From these, the relative intensities, 100 $I/I_o$, where $I_o$ is the intensity of the strongest line or peak, and $d$ (obs.), the interplanar spacing in Angstron units, corresponding to the recorded lines, were calculated.

It should be understood that this X-ray diffraction pattern is characteristic of all the species of ZSM-11 zeolites. Ion exchange of the sodium ion with cations reveals substantially the same pattern with some minor shifts in interplanar spacing and variation in relative intensity. Other minor variations can occur depending on the silicon to aluminum ratio of the particular sample, as well as if it has been subjected to thermal treatment.

In the present method of preparing a ZSM-11 crystalline aluminosilicate zeolite, a reaction mixture is prepared comprising sources of alkali metal, alumina, silica, alkylenediamine cations, and water. The reaction mixture has the following composition, expressed in terms of mole ratios of oxides:

| | Broad | Preferred |
| --- | --- | --- |
| $SiO_2/Al_2O_3$ | = 10–1000 | 20–200 |
| $H_2O/SiO_2$ | = 5–200 | 20–60 |
| $OH^-/SiO_2$ | = $10^{-10}$–1.0 | $10^{-6}$–0.6 |
| $M/SiO_2$ | = 0.1–2.0 | 0.2–1.0 |
| $R/SiO_2$ | = 0.01–2.0 | 0.1–1.0 | wherein M is an alkali metal ion, preferably sodium, and R is alkylenediamine having from 7 to 12 carbon atoms, preferably a polymethylenediamine of the general formula $H_2N-(CH_2)_m-NH_2$ wherein m is an integer of from 7 to 12, and more preferably 7 to 10. The reaction mixture is maintained at a temperature of from about 50° C to about 250° C for a period of time of from about 3 hours to about 180 days until crystals of ZSM-11 are formed. A more preferred temperature range is from about 80° C to about 200° C for a period of time at a temperature within such preferred range being from about 3 hours to about 30 days.

It is recalled that in calculating the mole ratio of hydroxide ions/silica, it is conventional to calculate hydroxide by summing moles of $OH^-$, whether added as NaOH, as quaternary Group VA element hydroxide (in the case of a conventional preparation), as sodium silicate (NaOH + SiO$_2$), as sodium aluminate (NaOH + Al$_2$O$_3$), or the like and to subtract from that sum any moles of acid added. Acid may be added simply as HCl, HNO$_3$, H$_2$SO$_4$, acetic acid, and the like or it may be added as an aluminum sulfate (Al$_2$O$_3$ + H$_2$SO$_4$), chloride (Al$_2$O$_3$ + HCl), nitrate (Al$_2$O$_3$ + HNO$_3$), etc. Each mole of Al$_2$O$_3$ is itself equivalent to 2 moles of acid in this calculation, since Al$_2$O$_3$ consumes 2 moles of hydroxide in its conversion to framework aluminate ion. In particular, no contribution is assigned to organic bases such as amines in this calculation. Amines present in reaction mixtures having an OH$^-$/SiO$_2$ ratio of 0.01 are protonated when further acid is added. Until said additional acid exceeds the amine present, the pH remains above 7.

In a conventional calculation, which does not consider amines, the total moles of acid could thereby exceed the moles of hydroxide initially present in said reaction mixture and subtraction would thereby lead to apparent "negative" OH$^-$/SiO$_2$ ratios. A negative ratio is, of course, not possible since the true moles of hydroxide (per liter) in an aqueous mixture are always positive and equal to $10^{-14}$ divided by the moles per liter of acid. Calculated from the true moles of hydroxide, the present invention would include an OH$^-$/SiO$_2$ range of about $10^{-10}$ to about 1.0.

For convenience, and to maintain the conventions established in describing reaction mixture compositions, we define a ratio of H$^+$(additional)/SiO$_2$, which is equal to the moles of H$^-$ added in excess of the moles OH$^-$ added in preparing the reaction mixture.

In the above reaction mixture composition, an optimum range in the OH$^-$/SiO$_2$ and R/SiO$_2$ ratios exists which is specific to each individual diamine. When larger amounts of diamine are effective, higher OH$^{-\lambda}$/SiO$_2$ ratios can be used; when the diamine is effective at low R/SiO$_2$ ratio, the optimum OH$^-$/SiO$_2$ ratio will generally be lower. These trends suggest that it is the protonated diamine which directs crystallization to ZSM-11.

The digestion of the gel particles is carried out until crystals form. The solid product is separated from the reaction medium, as by cooling the whole to room temperature, filtering and water washing.

In addition to providing a low-sodium ZSM-11 which can be used as a catalyst without intermediate exchange, it is interesting to note that the present method of preparation of ZSM-11 also provides the benefit of being lower cost than conventional preparation technique since the template materials for use herein are substantially lower cost than the conventional template materials. The zeolite product, therefore, is also of lower cost than conventionally prepared ZSM-11.

The composition for the synthesis of synthetic ZSM-11 can be prepared utilizing materials which can supply the appropriate oxide. Such materials include aluminates, alumina, silicates, silica hydrosol, silica gel, silicic acid and hydroxides. It will be understood that each oxide component utilized in the reaction mixture for preparing ZSM-11 can be supplied by one or more essential reactants and they can be mixed together in any order. For example, any oxide can be supplied by an aqueous solution, sodium hydroxide or by an aqueous solution of a suitable silicate; the alkylenediamine cation can be supplied by a compound of that cation, such as, for example, a salt, as well as by the indicated diamine. The reaction mixture can be prepared either batchwise or continuously. Crystal size and crystallization time of the ZSM-11 composition will vary with the nature of the reaction mixture employed.

The ZSM-11 composition as prepared hereby has the characteristic X-ray diffraction pattern of conventionally prepared ZSM-11, the values of which are set forth in Table I.

Even though the presently prepared ZSM-11 has an extremely low amount of alkali metal, e.g. sodium, ions, as synthesized, and therefore can be utilized as catalytic material for a number of hydrocarbon conversion reactions substantially as synthesized, the original alkali metal cations of the as synthesized ZSM-11 can be replaced in accordance with techniques well known in the art, at least in part, by ion exchange with other cations. Preferred replacing cations include metal ions, ammonium ions, hydrogen ions and mixtures thereof. Particularly preferred cations are those which render the zeolite catalytically active especially for hydrocarbon conversion. These include hydrogen, rare earth metals, aluminum, metals of Groups IIA, IIIB, IVB, VIB, VIII, IB, IIB, IIIA, IVA. Of the replacing metallic cations, particular preference is given to cations of metals such as rare earth, Mn, Ca, Mg, Zn, Cd, Pd, Ni, Ti, Al, Sn, Fe and Co.

A typical ion exchange technique would be to contact the synthetic ZSM-11 zeolite with a salt of the desired replacing cation or cations. Although a wide variety of salts can be employed, particular preference is given to chlorides, nitrates and sulfates.

Representative ion exchange techniques are disclosed in a wide variety of patents including U.S. Pat. Nos. 3,140,249; 3,140,251; and 3,140,253.

Following contact with the salt solution of the desired replacing cation, the zeolite is then preferably washed with water and dried at a temperature ranging from 150° F to about 600° F and thereafter may be calcined in air or other inert gas at temperatures ranging from about 500° F to 1500° F for periods of time ranging from 1 to 48 hours or more to produce a catalytically-active thermal decomposition product thereof.

Regardless of the cation replacing the cations in the synthesized form of the ZSM-11, the spatial arrangement of the aluminum, silicon and oxygen atoms which form the basic crystal lattices of ZSM-11 remains essentially unchanged by the described replacement of the original cations as determined by taking an X-ray powder diffraction pattern of the ion-exchanged material.

The hereby prepared zeolite ZSM-11 may be used in a wide variety of organic compound, e.g. hydrocarbon compounds and oxygenates such as methanol, conversion processes. Such processes include, for example, alkylation of aromatics with olefins, aromatization of normally gaseous olefins and paraffins, aromatization of normally liquid low molecular weight paraffins and olefins, isomerization of aromatics, paraffins and olefins, disproportionation of aromatics, transalkylation of aromatics, oligomerization of olefins and cracking and hydrocracking. All of the foregoing catalytic processes are of value since they result in upgrading of the organic charge being processed.

Synthetic ZSM-11 zeolites prepared in accordance hereto can be used either in the organic cation or alkali metal form and hydrogen form or another univalent or multivalent cationic form. They can also be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such components can be exchanged into the composition, impregnated therein or physically intimately admixed therewith. Such components can be impregnated in or on to ZSM-11 such as, for example, by, in the case of platinum, treating the zeolite with a platinum metal-containing ion. Thus, suitable platinum compounds for this purpose include chloroplatinic acid, platinous chloride and various compounds containing the platinum amine complex. Combinations of metals and methods for their introduction can also be used.

The aluminosilicate prepared by the instant invention is formed in a wide variety of particle sizes. Generally speaking, the particles can be in the form of a powder, a granule, or a molded product, such as extrudate having particle size sufficient to pass through a 2 mesh (Tyler) screen and be retained on a 400 mesh (Tyler) screen. In cases where the catalyst is molded, such as by extrusion, the aluminosilicate can be extruded before drying or dried or partially and then extruded.

In the case of many catalysts, it is desired to incorporate the ZSM-11 hereby prepared with another material resistant to the temperatures and other conditions employed in organic conversion processes. Such matrix materials include active and inactive materials and synthetic or naturally occurring zeolites as well as inorganic materials such as clays, silica and/or metal oxides. The latter may be either naturally occurring or in the form of gelatinous precipitates, sols or gels including mixtures of silica and metal oxides. Use of a material in conjunction with the ZSM-11 i.e. combined therewith, which is active, tends to improve the conversion and/or selectivity of the catalyst in certain organic conversion processes. Inactive materials suitably serve as diluents to control the amount of conversion in a given process so that products can be obtained economically and orderly without employing other means for controlling the rate of reaction. Frequently, zeolite materials have been incorporated into naturally occurring clays, e.g. bentonite and kaolin. These materials, i.e. clays, oxides, etc., function, in part, as binders for the catalyst. It is desirable to provide a catalyst having good crush strength, because in a petroleum refinery the catalyst is often subjected to rough handling, which tends to break the catalyst down into powder-like materials which cause problems in processing.

Naturally occurring clays which can be composited with the hereby synthesized ZSM-11 catalyst include the montmorillonite and kaolin families which include the sub-bentonites, and the kaolins commonly known as Dixie, McNammee, Georgia and Florida clays or others in which the main mineral constituent is halloysite, kaolinite, dickite, nacrite, or anauxite. Such clays can be used in the raw state or intially subjected to calcination, acid treatment or chemical modification.

In addition to the foregoing materials, the ZSM-11 catalyst hereby synthesized can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used. The relative proportions of finely divided crystalline aluminosilicate ZSM-11 and inorganic oxide gel matrix vary widely with the crystalline aluminosilicate content ranging from about 1 to about 90 percent by weight and more usually in the range of about 2 to about 50 percent by weight of the composite.

For conversion of organic compounds in general, the organic compound or feedstock containing same may be contacted with a catalyst containing the hereby prepared zeolite ZSM-11, commonly with a silica/alumina mole ratio in the range of from about 20 to about 200, at a temperature between about 100° F and about 1400° F, a pressure between about atmospheric and about 200 atmospheres, a hydrogen/organic compound mole ratio of between 0 and about 80, and a weight hourly space velocity (WHSV) of from about 0.1 hr$^{-1}$ to about 1000 hr$^{-1}$.

More specifically, when said conversion involves polymerization of olefin-containing liquid or gaseous feedstocks the temperature will be between about 500° F and about 900° F, the pressure will be from about atmospheric to about 50 atmospheres and the WHSV will be from about 0.5 hr$^{-1}$ to about 50 hr$^{-1}$. When said conversion is aromatization of gaseous or liquid feedstocks which may be olefinic or paraffinic with or without aromatics present, the temperature will be from about 800° F to about 1200° F, the pressure will be from about atmospheric to about 10 atmospheres and the WHSV will be from about 0.1 hr$^{-1}$ to about 10 hr$^{-1}$. When said conversion is the alkylation of aromatics, such as benzene or toluene, with an alkylating agent of an olefin or alcohol, reaction conditions will include a temperature of from about 400° F to about 1000° F, a pressure of from about atmospheric to about 60 atmospheres, a WHSV of from about 0.5 hr$^{-1}$ to about 50 hr$^{-1}$ and an aromatic compound/alkylating agent mole ratio of from about 2 to about 200. When said conversion is isomerization of aromatics such as xylenes, reaction conditions will include a temperature of from about 300°–900° F, a pressure of from about 1–60 atmospheres, and a WHSV of from about 0.2 hr$^{-1}$ to about 100 hr$^{-1}$. When said conversion is isomerization of paraffins or olefins, reaction conditions will include a temperature of from about 100°–700° F, a pressure of from about 1–60 atmospheres, and a WHSV of from about 0.1 hr$^{-1}$ to about 2 hr$^{-1}$. When said conversion is disproportionation of aromatics, such as toluene, reaction conditions will include a temperature of from about 600°–1100° F, a pressure of from about 1–50 atmospheres, and a WHSV of from about 0.5 hr$^{-1}$ to about 20 hr$^{-1}$. When said conversion is transalkylation of aromatics, such as benzene, with alkylaromatics, such as trimethylbenzenes, reaction conditions will include a temperature of from about 500°–1100° F, a pressure of from about 1–50 atmospheres, and a WHSV of from about 0.5 hr$^{-1}$ to about 20 hr$^{-1}$. When said conversion is oligomerization of olefins, such as propylene, reaction conditions will include a temperature of from about 500°–1100° F, a pressure of from about 1–50 atmospheres, and a WHSV of from about 0.1 hr$^{-1}$ to about 1000 hr$^{-1}$. When said conversion is cracking of a gas oil or a residual oil, reaction conditions will include a temperature of from about 600–1400° F, a pressure of from about 1–10 atmospheres, and a WHSV of from about 0.5 hr$^{-1}$ to about 50 hr$^{-1}$. When said conversion is hydrocracking of hydrocarbon-containing feedstocks, such as resids or heavy petroleum stocks, reaction conditions will include a temperature of from about 400°–850° F, a pressure of from about 10–200 atmospheres, a WHSV of from about 0.1 hr$^{-1}$ to about 10 hr$^{-1}$ and a H$_2$/hydrocarbon mole ratio of from 2–80.

In order to more fully illustrate the nature of the invention and the manner of practicing same, the following examples are presented.

EXAMPLES 1-29

Crystallizations were carried out at 160° C in both static and stirred and employed Q-brand sodium silicate (27.8% SiO$_2$, 8.42% Na$_2$O) as a source of silica and Al$_2$(SO$_4$)$_3$.16H$_2$O as a source of alumina. Reaction mixture compositions are desribed by the mole ratios SiO$_2$/Al$_2$O$_3$, H$_2$O/SiO$_2$, OH$^-$/SiO$_2$, Na/SiO$_2$, and R/SiO$_2$, where R is moles of alkylenediamine, in each instance being of the formula H$_2$N—(CH$_2$)$_m$—NH$_2$ where $m$ is from 4 to 12, and where each mole of Al$_2$O$_3$ is considered to consume two moles of OH$^-$ on conversion to framework AlO$_2-$. Moles of OH$^-$ are defined as moles of OH$^-$ added less any moles of mineral acid (H$^+$) added to the mixture. The pH of all reaction mixtures was above 7.

Table II records the results of crystallization experiments conducted at 160° C in a stirred system. From these data one observes that crystallization shifted from other zeolites to ZSM-11 and the diamine chain length increased from six carbon atoms to seven carbon atoms. Transition points were reached at C$_5$ and C$_7$. At C$_5$ alkylenediamine the product ZSM-35 cage appeared unable to accommodate the protonated (note low OH$^{-\lambda}$/SiO$_2$) diamine so that crystallization was directed to ZSM-5. Similarly, in the interval C$_7$–C$_{12}$ alkylenediamines, ZSM-11 resulted. Crystallization with C$_7$–C$_{10}$ alkylenediamines were a particularly efficient route to ZSM-11.

In Table III are recorded detailed runs at 160° C and at 100° C showing that the same general trends pertain in static crystallizations. These runs tend to concentrate in the low OH$^-$/SiO$_2$ range, compatible with the need to protonate an amine to render it both soluble and effective as a template. The results exhibit a scatter not found with the stirred crystallizations and suggestive of mixing problems, perhaps even partial phase separation, with the longer alkyl chains.

Analytical data for several of the ZSM-11 products relative to product composition is listed in Table IV.

TABLE II

Crystallization Experiments at 160° C in Stirred System

| Example | SiO$_2$/Al$_2$O$_3$ | H$_2$O/SiO$_2$ | OH$^-$/SiO$_2$ | R | R/SiO$_2$ | H$^+$(add'l)/SiO$_2$ | Days | Product |
|---|---|---|---|---|---|---|---|---|
| 1 | 15 | 39 | 0.01 | C$_4$DN[b] | 0.11 | 0 | 7 | 95% ZSM-35 |
| 2 | 30 | 40 | <0.01 | C$_5$DN | 0.29 | 0 | 3 | 75% ZSM-5 |
| 3 | 90 | 40 | 0.32 | C$_5$DN | 0.59 | 0 | 3 | 100% ZSM-5 |
| 4 | 90 | 40 | <0.01 | C$_6$DN | 0.29 | 0 | 3 | 100% ZSM-5 |
| 5 | 90 | 40 | <0.01 | C$_7$DN | 0.22 | 0 | 10 | 95% ZSM-11 |
| 6 | 90 | 40 | <0.01 | C$_8$DN | 0.29 | 0 | 3 | 100% ZSM-11 |
| 7 | 90 | 40 | <0.01 | C$_9$DN | 0.29 | 0 | 3 | 100% ZSM-11 |
| 8 | 90 | 40 | <0.01 | C$_{10}$DN | 0.29 | 0 | 3 | 95% ZSM-11 |
| 9 | 90 | 40 | <0.01 | C$_{12}$DN | 0.29 | 0 | 3 | 65% ZSM-11 |

[a] Na/SiO$_2$ = 0.59
[b] DN = diamine

TABLE III

Crystallization Experiments in Static System[a]

| Example | SiO$_2$/Al$_2$O$_3$ | H$_2$O/SiO$_2$ | OH$^-$/SiO$_2$ | R | R/SiO$_2$ | H$^+$(add'l)/SiO$_2$ | Days | Product |
|---|---|---|---|---|---|---|---|---|
| 10 | 30 | 40 | 0.32 | C$_3$DN[c] | 0.68 | 0 | 3 | 100% ZSM-35 |
| 11 | 30 | 40 | 0.32 | C$_4$DN | 0.68 | 0 | 3 | 95% ZSM-35 |
| 12 | 30 | 40 | <0.01 | C$_5$DN | 0.59 | 0 | 3 | 60% ZSM-5 + alpha-Quartz |
| 13 | 90 | 40 | <0.01 | C$_6$DN | 0.14 | 0 | 3 | 98% ZSM-5 |
| 14 | 90 | 40 | <0.01 | C$_6$DN | 0.29 | 0 | 3 | 80% ZSM-5 + alpha-Quartz |
| 15 | 30 | 40 | <0.01 | C$_6$DN | 0.59 | 0 | 3 | 60% ZSM-5 |
| 16 | 90 | 40 | <0.01 | C$_7$DN | 0.29 | 0 | 6 | 45% ZSM-5 + alpha-Quartz |
| 17 | 30 | 40 | <0.01 | C$_7$DN | 0.29 | 0 | 6 | 25% ZSM-11 |
| 18 | 10 | 40 | <0.01 | C$_7$DN | 1.0 | 0.22 | 3 | 50% ZSM-11 |
| 19 | 90 | 40 | <0.01 | C$_8$DN | 0.29 | 0 | 4 | 90% ZSM-11 + alpha-Quartz |
| 20 | 10 | 40 | <0.01 | C$_8$DN | 1.0 | 0.22 | 4 | 15% ZSM-11 |
| 21 | 90 | 40 | <0.01 | C$_9$DN | 0.29 | 0 | 4 | 70% ZSM-11 + alpha-Quartz |
| 22 | 10 | 40 | <0.01 | C$_9$DN | 1.0 | 0.22 | 4 | 20% ZSM-11 |
| 23 | 90 | 40 | <0.01 | C$_{10}$DN | 0.29 | 0 | 4 | 20% ZSM-11 |
| 24 | 90 | 40 | <0.01 | C$_{12}$DN | 0.29 | 0 | 3 | 95% ZSM-5 |
| 25 | 90 | 40 | 0.32 | C$_{12}$DN[c] | 0.59 | 0 | 3 | 95% ZSM-5 |
| 26 | 30 | 40 | 0.32 | C$_{12}$DN | 0.29 | 0 | 3 | 35% ZSM-5 |
| 27 | 30 | 40 | <0.01 | C$_{12}$DN | 0.29 | 0 | 3 | 55% ZSM-11 |
| 28 | 90 | 40 | <0.01 | C$_7$DN | 0.29 | 0 | 67 | 75% ZSM-11 |
| 29 | 90 | 40 | <0.01 | C$_9$DN | 0.29 | 0 | 67 | 60% ZSM-11 |

[a] Crystallizations for examples 10–27 were conducted at 160° C; for examples 28 and 29 at 100° C.
[b] Na/SiO$_2$ = 0.59
[c] DN = diamine

TABLE IV

Analytical Data for ZSM-11 Products

| Ex. | SiO$_2$/Al$_2$O$_3$ | Al/uc | Na/uc | N/uc | C/N | molecules/uc |
|---|---|---|---|---|---|---|
| 6 | 65.9 | 2.83 | 1.23 | 9.26 | 5.22 | 6.0 C$_8$DN |
| 19 | 73.0 | 2.56 | 1.08 | 3.16 | 11.4 | 4.5 C$_8$DN |
| 21 | 115.2 | 1.64 | 0.71 | 4.07 | 9.76 | 4.4 C$_9$DN |
| 8 | 75.7 | 2.47 | 0.47 | 6.92 | 6.17 | 4.2 C$_{10}$DN |

*Unit cell (uc) contains 96 Si + Al tetrahedra

EXAMPLE 30

A sample of zeolite ZSM-11 prepared as in Example 6 is calcined at 1000° F for 2 hours, contacted with ammonium chloride solution to effect ammonium exchange for residual sodium, dried at 200° F for 4 hours and then calcined at 1000° F for 2 hours. After sizing to 60/80 mesh, the zeolite's catalytic activity is measured by contact with a five-component feedstock comprising equal parts by weight of n-hexane, 3-methylpentane, 2,3-dimethylbutane, benzene and toluene at contact conditions of 800° F, 200 psig, a hydrogen/hydrocarbon mole ratio of 3 and a WHSV of 3 $hr^{-1}$. This test demonstrates simultaneously paraffin cracking, aromatization and aromatics alkylation and interconversion activity of the zeolite. The ratio of rate constants for n-hexane and 3-methylpentane conversion generated by this test is 2.3. Further demonstrated here is that 10% of the cracked paraffin fragments react with available aromatics in the feedstock to produce alkylaromatics with benzene, rather than toluene, being preferentially alkylated.

What is claimed is:

1. A synthetic crystalline aluminosilicate zeolite having a formula in terms of mole ratios of oxides in the anhydrous state as follows:

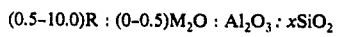

$(0.5-10.0)R : (0-0.5)M_2O : Al_2O_3 : xSiO_2$ wherein M is an alkali metal ion, R is an alkylenediamine having from 7 to 12 carbon atoms or an organic cation derived therefrom, and $x$ is from 10 to 1000, and having the X-ray powder diffraction pattern substantially as set forth in Table I of the specification.

2. The zeolite of claim 1 wherein $x$ is from about 20 to about 200.

3. The zeolite of claim 1 wherein said alkali metal is sodium and said alkylenediamine is a polymethylenediamine of the formula $H_2N—(CH_2)_m—NH_2$ wherein m is an integer of from 7 to 12.

4. The zeolite of claim 3 wherein $x$ is from about 20 to about 200.

5. The zeolite of claim 3 wherein $m$ is an integer of from 7 to 10.

6. A zeolite comprising the zeolite of claim 1 having its original alkali metal cations replaced, at least in part, by ion exchange with a cation or a mixture of cations selected from the group consisting of hydrogen and hydrogen precursors, rare earth metals, and metals from Groups IIA, IIIA, IVA, IB, IIB, IIIB, IVB, VIB and VIII of the Periodic Table of Elements.

7. A zeolite comprising the zeolite of claim 2 having its original alkali metal cations replaced, at least in part, by ion exchange with a cation or a mixture of cations selected from the group consisting of hydrogen and hydrogen precursors, rare earth metals, and metals from Groups IIA, IIIA, IVA, IB, IIB, IIIB, IVB, VIB and VIII of the Periodic Table of Elements.

8. A zeolite comprising the zeolite of claim 3 having its original alkali metal cations replaced, at least in part, by ion exchange with a cation or a mixture of cations selected from the group consisting of hydrogen and hydrogen precursors, rare earth metals, and metals from Groups IIA, IIIA, IVA, IB, IIB, IIIB, IVB, VIB and VIII of the Periodic Table of Elements.

9. A zeolite comprising the zeolite of claim 4 having its original alkali metal cations replaced, at least in part, by ion exchange with a cation or a mixture of cations selected from the group consisting of hydrogen and hydrogen precursors, rare earth metals, and metals from Groups IIA, IIIA, IVA, IB, IIB, IIIB, IVB, VIB and VIII of the Periodic Table of Elements.

10. A zeolite comprising the zeolite of claim 5 having its original alkali metal cations replaced, at least in part, by ion exchange with a cation or a mixture of cations selected from the group consisting of hydrogen and hydrogen precursors, rare earth metals, and metals from Groups IIA, IIIA, IVA, IB, IIB, IIIB, IVB, VIB and VIII of the Periodic Table of Elements.

11. The zeolite of claim 6 wherein said replacing cation is hydrogen or a hydrogen precursor.

12. The zeolite of claim 7 wherein said replacing cation is hydrogen or a hydrogen precursor.

13. The zeolite of claim 8 wherein said replacing cation is hydrogen or a hydrogen precursor.

14. The zeolite of claim 9 wherein said replacing cation is hydrogen or a hydrogen precursor.

15. The zeolite of claim 10 wherein said replacing cation is hydrogen or a hydrogen precursor.

16. The method for preparing the crystalline aluminosilicate zeolite defined in claim 1 which comprises preparing a mixture containing sources of an alkali metal, an oxide of aluminum, an oxide of silicon, water and an alkylenediamine having from 7 to 12 carbon atoms and having a composition, in terms of mole ratios of oxides, within the following ranges:

$SiO_2/Al_2O_3 = 10-1000$
$H_2O/SiO_2 = 5 \propto 200$
$OH^-/SiO_2 = 10^{-10}-1.0$
$M/SiO_2 = 0.1-2.0$
$R/SiO_2 = 0.01-2.0$ wherein R is an alkylenediamine having 7 to 12 carbon atoms, and M is an alkali metal ion, and maintaining the mixture at a temperature of at least 50° C until the crystals of said zeolite are formed.

17. The method according to claim 16 wherein the temperature is maintained between about 50° C and about 250° C.

* * * * *

UNITED STATES PATENT AND TRADEMARK OFFICE
CERTIFICATE OF CORRECTION

PATENT NO. : 4,108,881
DATED : August 22, 1978
INVENTOR(S) : LOUIS DEANE ROLLMAN and ERNEST WILLIAM VALYOCSIK It is certified that error appears in the above-identified patent and that said Letters Patent are hereby corrected as shown below:

Column 3, line 32, "to the moles of $H^-$" should read
--to the moles of $H^+$--.

Column 7, line 9, "static and stirred and employed" should read
--static and stirred systems and employed--.

Column 10, line 44, "$H_2O/SiO_2 = 5 \propto 200$" should read
--$H_2O/SiO_2 = 5-200$--.

Signed and Sealed this

Fifth Day of June 1979

[SEAL]

Attest:

RUTH C. MASON
Attesting Officer

DONALD W. BANNER
Commissioner of Patents and Trademarks